United States Patent [19]

Stulbach

[11] Patent Number: 5,207,221

[45] Date of Patent: May 4, 1993

[54] AERATED RESPIRATORY MOUTHPIECE (ORAL GUM SEPARATOR)

[76] Inventor: Nathan H. Stulbach, 40 Brighton First Rd., Brooklyn, N.Y. 11235

[21] Appl. No.: 715,021

[22] Filed: Jun. 13, 1991

Related U.S. Application Data

[63] Continuation of Ser. No. 382,174, Jun. 26, 1989, abandoned.

[51] Int. Cl.⁵ .............................................. A62B 18/08
[52] U.S. Cl. .......................... 128/206.29; 128/200.26
[58] Field of Search ................... 128/200.26, 206.29, 128/207.14, 207.15, 201.11, 848

[56] References Cited

U.S. PATENT DOCUMENTS

| | | | |
|---|---|---|---|
| 690,663 | 1/1902 | Pratt | 128/201.11 |
| 770,013 | 9/1904 | Linn | 128/206.29 |
| 838,434 | 12/1906 | Morgan | 128/206.29 |
| 893,213 | 7/1908 | Whiteway | 128/206.29 |
| 1,362,766 | 12/1920 | McGargill | 128/206.29 |
| 1,418,182 | 5/1922 | Tabor | 128/206.29 |
| 1,476,194 | 12/1923 | Dismond | 128/206.29 |
| 1,978,994 | 10/1934 | Fortunato | 128/206.29 |
| 2,385,938 | 10/1945 | Pierce | 128/206.29 |
| 3,020,911 | 2/1962 | Girden | 128/206.29 |
| 4,098,270 | 7/1978 | Dolby | 128/206.29 |
| 4,170,230 | 10/1979 | Nelson | 128/848 |
| 4,261,354 | 4/1981 | Nelson | 128/848 |
| 4,895,143 | 1/1990 | Fisher | 128/206.29 |
| 5,046,512 | 9/1991 | Murchie | 128/848 |

*Primary Examiner*—David A. Wiecking
*Assistant Examiner*—Aaron J. Lewis
*Attorney, Agent, or Firm*—S. C. Yuter

[57] ABSTRACT

A respiratory mouthpiece for a toothless person comprising a conduit having an outside open end and an inside open end and adapted to pass untreated atmospheric air from the outside open end to the inside open end. A shield is connected to the conduit adjacent its outside open end to prevent the mouthpiece from being swallowed when the mouthpiece is inserted between the gums of a toothless person. A plurality of perforations in the outer surface of the conduit increase the distribution of inhaled air in the oral cavity. An air filter connected inside the conduit intermediate its open ends purifies the inhaled air from possible pollutants.

16 Claims, 1 Drawing Sheet

AERATED RESPIRATORY MOUTHPIECE (ORAL GUM SEPARATOR)

This application is a continuation of application Ser. No. 07/382,174 filed Jun. 26, 1989 now abandoned.

BACKGROUND OF THE INVENTION

1. Field of the Invention

This invention generally relates to respiratory mouthpieces, and more particularly to aerated respiratory mouthpieces for separating the gums of toothless persons so they can breath ambient air.

2. Description of the Related Art

Mouthpieces for controlling the flow of gases into the respiratory system are well known. For example, U.S. Pat. No. 4,895,143, filed Dec. 21, 1987 and granted Jan. 23, 1990, discloses mouthpieces for controlling the communication of gas entering and leaving the respiratory system by sealing off gases in the ambient environment. However, such mouthpieces require teeth as part of the sealing mechanism and are not useful for toothless persons.

Other devices for controlling the flow of gases into the respiratory system are essentially hoods or gas masks. Examples of such devices are disclosed in U.S. Pat. No. 4,098,270 granted Jul. 4, 1978 for a Smoke Mask Apparatus; U.S. Pat. No. 3,020,911 granted Feb. 13, 1962 for a Mask; U.S. Pat. No. 2,385,938 granted Oct. 2, 1945 for a Gas Filter; U.S. Pat. No. 1,978,994 granted Oct. 30, 1934 for a Protective Helmet; U.S. Pat. No. 1,362,766 granted Dec. 21, 1920 for a Gas Mask; U.S. Pat. No. 893,213 granted Jul. 14, 1908 for a Respirator, and U.S. Pat. No. 838,434 granted Dec. 11, 1906 for a Respirator. The purpose of these masks is to prevent the inhalation of air or gases in the ambient environment rather than for breathing ambient air.

Other devices for controlling the flow of gases into the respiratory system are essentially inhalers for medicating respiratory passages with medicated ambient air. Examples of such devices are U.S. Pat. No. 1,476,194 granted Dec. 4, 1923 for an Inhaler; U.S. Pat. No. 1,418,182 granted May 30, 1922 for an Inhaler, and U.S. Pat. No. 770,013 granted Sep. 13, 1904 for an Inhaler. These devices are for changing the characteristics of inhaled air rather than for permitting inhalation of unmedicated ambient air.

SUMMARY OF THE INVENTION

It is the main object of the invention to provide a respiratory mouthpiece for toothless persons in order to secure a continuous supply of oxygen to the oral cavity during any time when the nasal air passages are completely obstructed.

It is another object of the invention to provide a respiratory mouthpiece for stabilizing the equilibrium of the nasal, oral and all other adjacent membrane and muscle tissues when a condition of toothlessness and the absence of normal dental articulation is prevailing in the oral cavity.

It is further object of the invention to provide a safe and inexpensive aerated respiratory mouthpiece.

Briefly, in accordance with the invention, these and other objects are achieved by a respiratory mouthpiece for a toothless person comprising a conduit having an outside open end and an inside open end which is adapted to pass untreated atmospheric air from the outside open end to the inside open end. A shield is connected to the conduit adjacent its outside open end to prevent the mouthpiece from being swallowed when the mouthpiece is inserted between the gums of a toothless person.

A feature of the invention is a plurality of perforations in the outer surface of the conduit to increase the distribution of inhaled air in the oral cavity.

Another feature of the invention is an air filter connected inside the conduit intermediate its open ends to purify the inhaled air from possible pollutants.

A principal advantage of the invention is that it can easily be used by a toothless infant to prevent asphyxiation when the nasal passages are blocked.

Other objects, features and advantages of the invention will be apparent from the following description of the preferred embodiments when read in connection with the figures of the drawings.

DESCRIPTION OF THE PREFERRED EMBODIMENTS

The respiratory mouthpiece, which also functions as an aerated respiratory oral gum separator, is of tubular, rectangular or other form. It is preferably made of latex, rubber or any plastic material and is comfortable to keep in a person's mouth. The respiratory mouthpiece measures about ¼ to 1¼ inches wide and about 1 to 1½ inches in length. Its purpose is to supplement a deficient dental articulation and to augment a failing inhalatory capability of the person using it.

Figure 1:
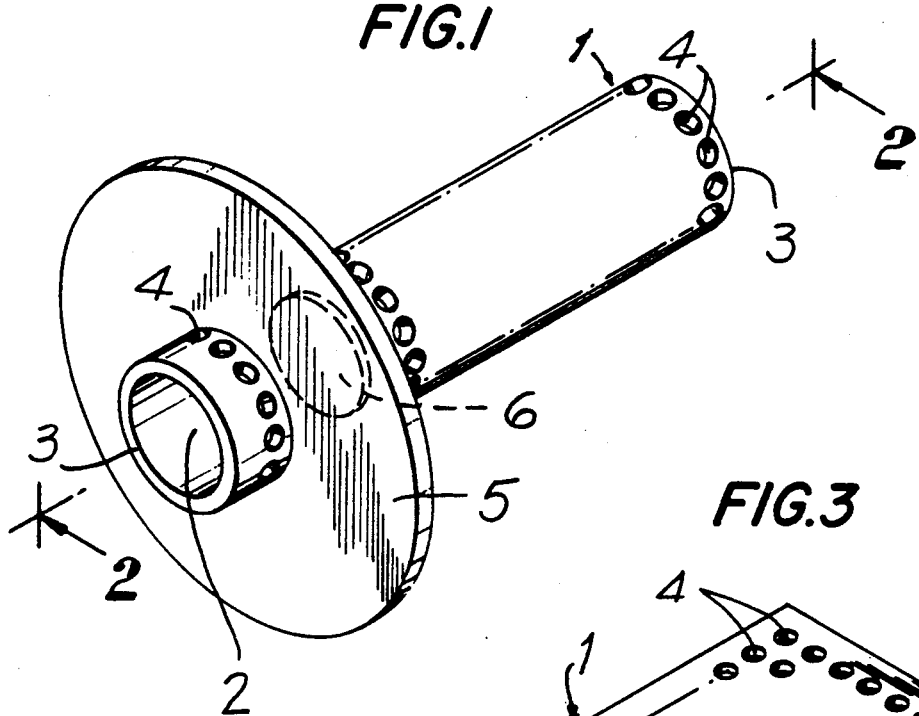
FIG. 1 is a schematic plan view of a respiratory mouthpiece in accordance with one embodiment of invention in which the conduit is tubular.

Referring to FIG. 1, the tubular respiratory mouthpiece comprises a conduit 1 having a hollow airway 2 through its entire length between its ends 3 to allow the entrance and flow of atmospheric air into the oral cavity and pulmonary organs of the person using it.

Conduit 1 has a multitude of little holes or perforations 4 all over its outer surface or wall on the portion which is inserted in a person's oral cavity. The purpose of perforations 4 is the thorough distribution of the inhaled ambient air in the oral channel.

A circular shield 5 is orthogonally connected to the outer surface of conduit 1 adjacent the outside end 3, preferably molded as part of the respiratory mouthpiece. When the mouthpiece is in use shield 5 is located in front of the lips and prevents accidental swallowing of the mouthpiece.

Inside conduit 1, fully crossing the airway, is a filter 6 to purify the inhaled atmospheric air from possible pollutants.

Figure 2:
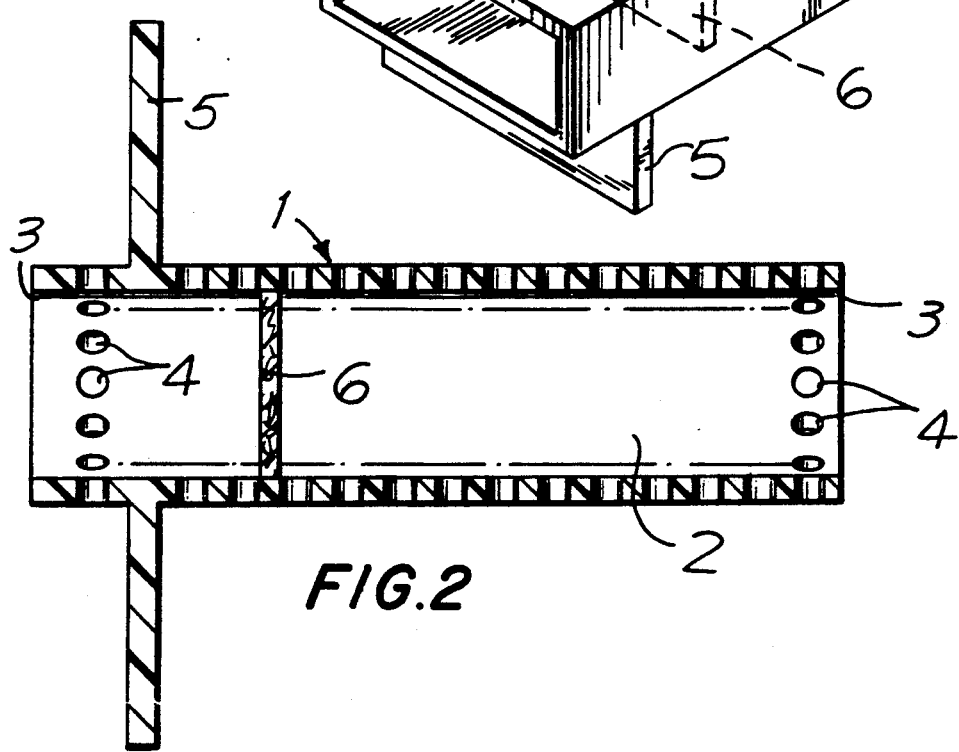
FIG. 2 is a side perspective view of another embodiment of the respiratory mouthpiece invention, the best mode, in which the conduit is rectangular in cross section.

Corresponding parts of the FIG. 2 rectangular embodiment of the respiratory mouthpiece invention bear the same reference characters as in the tubular mouthpiece of FIG. 1 and function in the same way.

Referring to FIG. 2, conduit 1 of the mouthpiece is in a flat shape; that is, it has a rectangular cross section. Shield 5 is rectangular in shape. Filter 6 is also rectangular in shape.

What is claimed is:

1. A respiratory mouthpiece for directly extending into the oral cavity of a toothless person comprising:

(A) a conduit having an outside open end and an inside open end and adapted to pass untreated atmospheric air from the outside open end to the inside open end; and
(B) a shield connected to said conduit adjacent the outside open end of said conduit having a size which prevents said shield from passing between the lips of a toothless person when said conduit is inserted between the gums of the toothless person;
(C) said conduit having a length such that the distance between said shield and said inside open end is sufficient so that said conduit can directly pass between the gums of the toothless person and directly extend into the oral cavity of the toothless person;
(D) wherein the wall of said conduit comprises a plurality of perforations to pass untreated atmospheric air to the inside of said conduit.

2. A respiratory mouthpiece according to claim 1 further comprising an air filter positioned inside said conduit intermediate said shield and its inside open end.

3. A respiratory mouthpiece according to claim 1 wherein said conduit is substantially circular in cross section.

4. A respiratory mouthpiece according to claim 3 further comprising an air filter positioned inside said conduit intermediate said shield and its inside open end.

5. A respiratory mouthpiece according to claim 1 wherein said conduit is rectangular in cross section.

6. A respiratory mouthpiece according to claim 1 wherein the width of said conduit is about $\frac{1}{4}$ to $1\frac{1}{4}$ inches.

7. A respiratory mouthpiece according to claim 1 wherein the length of said conduit is about 1 to $1\frac{1}{2}$ inches.

8. A respiratory mouthpiece according to claim 1 wherein said shield is orthogonally connected to said conduit.

9. A respiratory mouthpiece according to claim 1 wherein said shield is circular.

10. A respiratory mouthpiece according to claim 9 further comprising an air filter positioned inside said conduit intermediate said shield and its inside open end.

11. A respiratory mouthpiece according to claim 1 wherein said conduit is made from a plastic material.

12. A respiratory mouthpiece according to claim 1 wherein said conduit is made from a flexible material.

13. A respiratory mouthpiece for directly extending into the oral cavity of a toothless person comprising:
(A) a conduit having an outside open end and an inside open end and adapted to pass untreated atmospheric air from the outside open end to the inside open end; and
(B) a shield connected to said conduit adjacent the outside open end of said conduit having a size which prevents said shield from passing between the lips of a toothless person when said conduit is inserted between the gums of the toothless person;
(C) said conduit having a length such that the distance between said shield and said inside open end is sufficient so that said conduit can directly pass between the gums of the toothless person and directly extend into the oral cavity of the toothless person;
(D) wherein said shield is substantially orthogonally connected to said conduit; and
(E) wherein the wall of said conduit comprises a plurality of perforations to pass untreated atmospheric air to the inside of said conduit.

14. A respiratory mouthpiece according to claim 13 further comprising an air filter positioned inside said conduit intermediate said shield and its inside open end.

15. A respiratory mouthpiece according to claim 13 wherein the length of said conduit is about 1 to $1\frac{1}{2}$ inches.

16. A respiratory mouthpiece according to claim 13 wherein said conduit is made from a plastic material.

* * * * *

UNITED STATES PATENT AND TRADEMARK OFFICE
CERTIFICATE OF CORRECTION

PATENT NO. : 5,207,221
DATED : May 4, 1993
INVENTOR(S) : Nathan Stulbach

It is certified that error appears in the above-identified patent and that said Letters Patent is hereby corrected as shown below:

Title Page, change the named Inventor to -- Nathan Stulbach --
(item 75)

Col. 2, line 20, change "a schematic plan" to -- an enlarged perspective --

Col. 2, after line 22, insert the following paragraph --FIG. 2 is a cross-sectional view of the respiratory mouthpiece of FIG. 1 along the line 2-2 --

Figure 3:
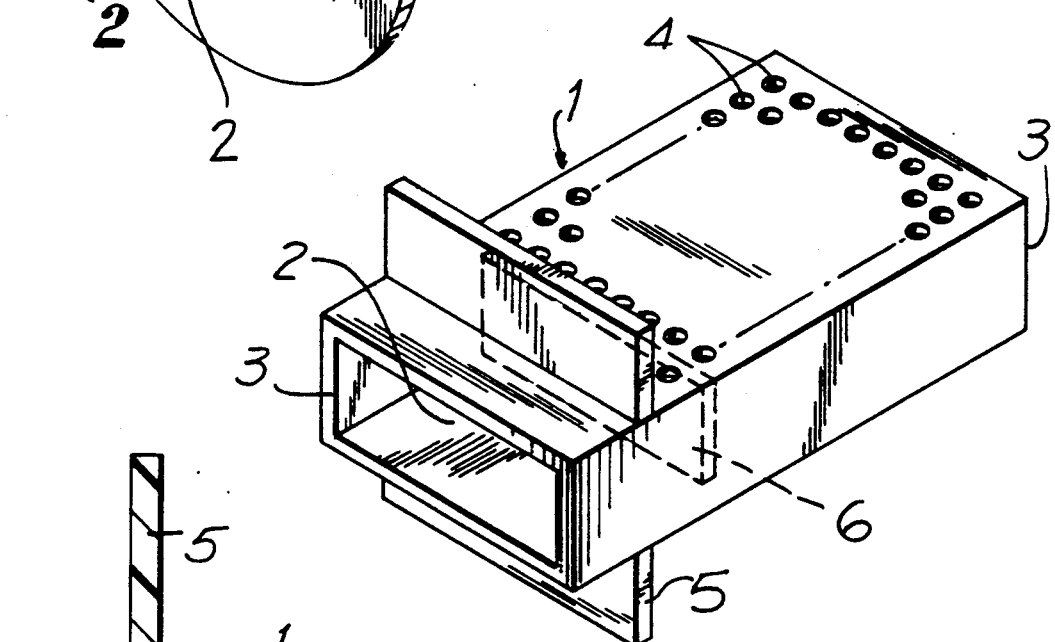

Col. 2, line 23, change "FIG. 2 is a side" to -- FIG. 3 is an enlarged --

Col. 2, line 39, change "FIG. 1" to -- FIGS. 1 and 2 --

Col. 2, line 58, change "FIG. 2" to -- FIG. 3 --

Col. 2, line 62, change "FIG. 2" to -- FIG. 3 -- .

Signed and Sealed this

Eleventh Day of January, 1994

*Attest:*

BRUCE LEHMAN

*Attesting Officer*    *Commissioner of Patents and Trademarks*